(12) United States Patent
Clarke et al.

(10) Patent No.: US 12,427,270 B2
(45) Date of Patent: Sep. 30, 2025

(54) INHALER FOR USE WITH A COMPLIANCE MONITOR

(71) Applicant: VECTURA DELIVERY DEVICES LIMITED, Wiltshire (GB)

(72) Inventors: Roger Clarke, Cambridgeshire (GB); Andreas Meliniotis, Cambridgeshire (GB); John Deamer, Cambridgeshire (GB); Darryl Cotton, Cambridgeshire (GB)

(73) Assignee: VECTURA DELIVERY DEVICES LIMITED (GB)

( * ) Notice: Subject to any disclaimer, the term of this patent is extended or adjusted under 35 U.S.C. 154(b) by 813 days.

(21) Appl. No.: 17/775,151

(22) PCT Filed: Nov. 17, 2020

(86) PCT No.: PCT/EP2020/082422
§ 371 (c)(1),
(2) Date: May 6, 2022

(87) PCT Pub. No.: WO2021/099324
PCT Pub. Date: May 27, 2021

(65) Prior Publication Data
US 2022/0395651 A1  Dec. 15, 2022

(30) Foreign Application Priority Data

Nov. 18, 2019 (EP) .................... 19209856
Nov. 18, 2019 (EP) .................... 19209857
Nov. 18, 2019 (EP) .................... 19209858

(51) Int. Cl.
*A61M 15/00* (2006.01)

(52) U.S. Cl.
CPC .... *A61M 15/0065* (2013.01); *A61M 15/0021* (2014.02); *A61M 15/0035* (2014.02);
(Continued)

(58) Field of Classification Search
CPC .......... A61M 15/0021; A61M 15/0065; A61M 2205/3331; A61M 2016/0027
See application file for complete search history.

(56) References Cited

U.S. PATENT DOCUMENTS

| 2005/0087473 A1 | 4/2005 | Fabricius et al. |
| 2007/0240712 A1 | 10/2007 | Fleming et al. |

(Continued)

FOREIGN PATENT DOCUMENTS

| CN | 102458543 A | 5/2012 |
| CN | 104080502 A | 10/2014 |

(Continued)

OTHER PUBLICATIONS

Notification of Transmittal of the International Preliminary Report on Patentability from corresponding International Application No. PCT/EP2020/082432, mailed on Feb. 25, 2022. International Search Report from corresponding International Application No. PCT/EP2020/082432, mailed Jan. 20, 2021. Written Opinion of the International Searching Authority from corresponding International Application No. PCT/EP2020/082432, mailed on Apr. 13, 2021.

(Continued)

*Primary Examiner* — Kendra D Carter
*Assistant Examiner* — Jaeick Jang
(74) *Attorney, Agent, or Firm* — Davidson Kappel LLC (57) ABSTRACT

A dry powder inhaler is provided. The inhaler is adapted for detachably mounting a compliance monitor having a pressure sensor. The inhaler has a housing comprising first and second shell parts, and a mouthpiece which defines an inhalation passage. An external surface of the housing has an orifice. A conduit from the orifice to the inhalation passage is formed by a channel in one of the shell parts and a corresponding channel cover in the other shell part. When the compliance monitor is mounted on the housing, the (Continued)

pressure sensor is adjacent to the orifice and is in fluid communication with the inhalation passage via the conduit.

17 Claims, 12 Drawing Sheets

(52) U.S. Cl.
CPC ................ *A61M 2202/064* (2013.01); *A61M 2205/3331* (2013.01)

(56) References Cited

U.S. PATENT DOCUMENTS

| | | |
|---|---|---|
| 2009/0020113 A1 | 1/2009 | Watanabe |
| 2010/0031956 A1 | 2/2010 | Pocock et al. |
| 2010/0192948 A1 | 8/2010 | Sutherland et al. |
| 2012/0145586 A1 | 6/2012 | Doyle et al. |
| 2014/0007875 A1* | 1/2014 | Berg ................ A61M 15/0016 128/203.15 |
| 2015/0112707 A1 | 4/2015 | Manice et al. |
| 2016/0256639 A1 | 9/2016 | Van Sickle et al. |
| 2017/0325734 A1 | 11/2017 | Sutherland et al. |
| 2019/0224426 A1 | 7/2019 | Farina et al. |
| 2019/0298942 A1 | 10/2019 | Koblenski et al. |
| 2020/0155773 A1* | 5/2020 | Zipkes ................ G16H 20/13 |

FOREIGN PATENT DOCUMENTS

| | | |
|---|---|---|
| CN | 105492057 A | 4/2016 |
| CN | 108472461 A | 8/2018 |
| CN | 108939228 | 12/2018 |
| EP | 1 521 609 B1 | 12/2009 |
| EP | 2 666 501 A1 | 11/2013 |
| EP | 3 552 647 A1 | 10/2019 |
| JP | 2000-508943 | 7/2000 |
| JP | 2005-538788 | 12/2005 |
| JP | 2011509727 | 3/2011 |
| JP | 2011212252 | 10/2011 |
| JP | 2014237011 | 12/2014 |
| RU | 2 163 819 C2 | 3/2001 |
| RU | 2 382 657 C1 | 2/2010 |
| RU | 2 618 931 C2 | 5/2017 |
| RU | 2 691 615 C2 | 6/2019 |
| RU | 2 696 147 C1 | 7/2019 |
| TW | 201620569 A | 6/2016 |
| WO | WO 1994/27555 | 12/1994 |
| WO | WO 1996/13294 | 5/1996 |
| WO | WO1997/040876 | 11/1997 |
| WO | WO 2001/58236 A2 | 8/2001 |
| WO | WO 2001/63368 A2 | 8/2001 |
| WO | WO 2001/68169 A1 | 9/2001 |
| WO | WO 2003/035508 A1 | 5/2003 |
| WO | WO 2003/063754 A1 | 8/2003 |
| WO | WO2003/090811 | 11/2003 |
| WO | WO 2003/095010 A2 | 11/2003 |
| WO | WO 2004/009470 A2 | 1/2004 |
| WO | WO2004/026378 | 4/2004 |
| WO | WO 2005/014089 A1 | 2/2005 |
| WO | WO 2005/037353 A1 | 4/2005 |
| WO | WO 2007/008858 A2 | 1/2007 |
| WO | WO 2007/012871 A1 | 2/2007 |
| WO | WO 2007/127359 A2 | 11/2007 |
| WO | WO2009/092592 | 7/2009 |
| WO | WO 2009/155581 A1 | 12/2009 |
| WO | WO 2010/036839 A2 | 4/2010 |
| WO | WO2010/135340 A2 | 11/2010 |
| WO | WO 2011/077414 A2 | 6/2011 |
| WO | WO 2011/130583 A2 | 10/2011 |
| WO | WO 2012/026963 A2 | 3/2012 |
| WO | WO 2012/041938 A2 | 4/2012 |
| WO | WO 2012/078804 A1 | 6/2012 |
| WO | WO 2012/085919 A2 | 6/2012 |
| WO | WO 2012/174552 A2 | 12/2012 |
| WO | WO 2013/043063 A1 | 3/2013 |
| WO | WO2013/036881 A2 | 4/2013 |
| WO | WO 2013/175176 A1 | 11/2013 |
| WO | WO 2013/175177 A1 | 11/2013 |
| WO | WO 2014/097294 A1 | 6/2014 |
| WO | WO 2014/147550 A1 | 9/2014 |
| WO | WO 2014/149691 A1 | 9/2014 |
| WO | WO 2014/204511 A2 | 12/2014 |
| WO | WO 2015/030610 A2 | 3/2015 |
| WO | WO 2016/001926 A1 | 1/2016 |
| WO | WO 2016/030521 A1 | 3/2016 |
| WO | WO 2016/033419 A1 | 3/2016 |
| WO | WO2016/043601 | 3/2016 |
| WO | WO2016/033421 A8 | 4/2016 |
| WO | WO2016/081294 A1 | 5/2016 |
| WO | WO 2016/156093 A1 | 10/2016 |
| WO | WO 2016/186859 A1 | 11/2016 |
| WO | WO 2016/187695 A1 | 12/2016 |
| WO | WO 2017/005605 A1 | 1/2017 |
| WO | WO2017/051389 A1 | 4/2017 |
| WO | WO2017/125853 A1 | 7/2017 |
| WO | WO2017/141194 A1 | 8/2017 |
| WO | WO 2018/051346 A1 | 3/2018 |
| WO | WO 2018/104268 A1 | 6/2018 |
| WO | WO 2018/138788 A1 | 8/2018 |
| WO | WO2019/021254 | 1/2019 |
| WO | WO2019/022620 | 1/2019 |

OTHER PUBLICATIONS

International Search Report from corresponding International Application No. PCT/EP2020/082432, mailed Jan. 20, 2021.
Written Opinion of the International Searching Authority from corresponding International Application No. PCT/EP2020/082432, mailed on Apr. 13, 2021.
Notification of Transmittal of the International Preliminary Report on Patentability from corresponding International Application No. PCT/EP2020/082422, mailed on Apr. 1, 2021.
International Search Report from corresponding International Application No. PCT/EP2020/082422, mailed Jan. 18, 2021.
Written Opinion of the International Searching Authority from corresponding International Application No. PCT/EP2020/082422, mailed on Jan. 18, 2021.
Notification of Transmittal of the International Preliminary Report on Patentability from corresponding International Application No. PCT/EP2020/082428, mailed on Feb. 24, 2022.
International Search Report from corresponding International Application No. PCT/EP2020/082428, mailed Jan. 14, 2021.
Written Opinion of the International Searching Authority from corresponding International Application No. PCT/EP2020/082428, mailed on Apr. 1, 2021.
Communication of a Notice of Opposition opposing EP4061453B1 dated May 28, 2024 including Opposition filed by PGA Intellectual Property.
Proprietor's Reply to the Grounds of Opposition in EP4061453 filed on Aug. 30, 2024.

* cited by examiner

INHALER FOR USE WITH A COMPLIANCE MONITOR

This application is a U.S. national phase application under 35 U.S.C. of § 371 of International Application No. PCT/EP2020/082422, filed Nov. 17, 2020, which claims priority of European Patent Application No. EP 19209856.4, filed Nov. 18, 2019, and European Patent Application No. EP 19209857.2, filed Nov. 18, 2019, and European Patent Application No. EP 19209858.0, filed Nov. 18, 2019.

TECHNICAL FIELD OF THE INVENTION

The present invention relates to an inhaler for dry powders containing one or more active substances for inhalation. In particular, the invention relates to an inhaler for use with a compliance monitor.

BACKGROUND TO THE INVENTION

Dry powder inhalers (DPIs) provide an attractive method for administering medicaments, for example to treat local diseases of the airway or to deliver drugs to the bloodstream via the lungs. The medicament is commonly provided as individual doses, such as a strip having a plurality of blisters, for example as disclosed in WO13/175177.

The efficacy of treatment is dependent on the patient using the inhaler correctly and as prescribed. Consequently, there is increasing interest in monitoring patient adherence and compliance. Adherence refers to the patient following the prescription, for example taking the prescribed number of doses per day, e.g. once or twice daily. Compliance refers to whether the patient uses their inhaler correctly. For example, most DPIs rely on the force of patient inhalation to entrain the powder and disperse it into particles that are small enough to reach the lungs. Consequently, an insufficiently strong or deep inhalation may lead to reduced dose delivery.

DPIs typically have a dose counter, either in the form of numbers printed onto the blister strip or as a separate mechanism which counts up or down each time the inhaler is actuated. While a dose counter can help patients and caregivers to monitor adherence, there is no means of determining whether the user has inhaled appropriately. So, when faced with a patient for whom no improvement can be seen, the doctor does not know whether a higher dose or a different medication is needed, or whether it is simply a result of the patient not using their inhaler correctly as prescribed. Therefore, devices have been developed that provide compliance information. For example, a pressure sensor can be used to monitor inhalation because the flow rate and total flow volume can be determined from the measured pressure as a function of time.

DPIs typically contain a month's supply of medication. Since compliance monitors usually contain expensive sensors, electronics etc., they are often provided as separate add-on modules which couple to the inhaler. Thus, when the medication in the inhaler has been used up, the compliance monitor can be detached and then re-attached to a new inhaler. The compliance monitor must not interfere with the patient's inhalation, so it is typically arranged to clip on to a side or base of the inhaler remote from the mouthpiece. Nonetheless, the pressure sensor must be connected with the mouthpiece or another part of the inhalation flow path. Thus a connecting tube, pipe or the like is required.

WO 16/033421 describes compliance monitoring modules for various types of inhaler in which a miniature pressure sensor is pneumatically coupled to the flow path of the inhaler through which the user inhales. A compliance monitor for a DPI is disclosed, in which the pressure sensor is connected to the inhaler via a capillary tube. However, this requires an additional component (the tube), which the user must connect correctly. This extra step could discourage patients from using the compliance monitor.

Thus there remains a need for improved inhalers and compliance monitors that are simple for the patient to use in order to contribute to better compliance, and that are also cost-effective to manufacture.

BRIEF DESCRIPTION OF THE INVENTION

The present invention addresses these problems. In a first aspect, the invention provides a dry powder inhaler adapted for detachably mounting a compliance monitor having a pressure sensor, the inhaler having a housing comprising first and second shell parts and a mouthpiece which defines an inhalation passage, wherein the housing has an orifice in an external surface and a conduit from the orifice to the inhalation passage, wherein the conduit is formed by a channel in one of the shell parts and a corresponding channel cover in the other shell part, in particular, in the second and first shell parts respectively.

The inhaler is designed for use with a removably attachable compliance monitor with a pressure sensor, so that when the compliance monitor is mounted on the housing, the pressure sensor is in fluid communication with the inhalation passage. The shell parts may be moulded plastic parts that can be welded together, so the inhaler is cost-effective to manufacture. In particular, since the conduit which connects the pressure sensor to the inhalation passage is built into the inhaler, there is no need for any extra components, such as tubes, which would increase the cost and complexity. Moreover, once the compliance monitor has been attached to the inhaler, no additional user steps are required.

The conduit may have a cross-sectional area of less than 5 mm$^2$, preferably less than 2 mm$^2$, such as about 1 mm$^2$.

The channel may have a ledge on each side. The ledges provide defined surfaces for welding the channel cover onto the channel. The channel cover may be formed as a protrusion. The protrusion and ledges may be welded together along their length. The height of the protrusion may be greater than the depth of the ledges and the width of the protrusion may be less than the width of the channel and ledges. This configuration provides interference material for welding and space for redistribution of the interference material as the weld is formed. This results in good welding so that the conduit is airtight along its length. The channel and channel cover are preferably not welded at the external surface of the inhaler. This prevents the formation of splay on the external surface, so that the surface is smooth and so that a leak-free face seal can be formed with the compliance monitor.

In one embodiment, the orifice is formed at the join between the shell parts.

In another embodiment the orifice is formed entirely within the second shell part. This has the advantage that the potential leak path along the unwelded surface joint does not communicate with the orifice, thereby ensuring that the conduit is airtight at the orifice. The channel may have a step near the orifice so that its depth is increased. This allows the channel to connect to the orifice which is spaced apart from the join between the shell parts, without increasing the cross-sectional area of the whole channel. An end ledge may be situated adjacent to the orifice on the inside of the second shell part which connects the ledges on each side of the channel. This allows a continuous weld to be formed around the channel at the orifice end which is entirely inside the housing. Consequently, the conduit is sealed at the orifice end whilst the external surface is perfectly smooth so that the compliance monitor can form a leak-free face seal.

In a specific embodiment, the inhaler comprises a compartment for a blister strip having a plurality of blisters which contain powdered medicament for inhalation, an indexing mechanism for moving the blister strip, a piercer which is mounted on the underside of the mouthpiece, and an actuator which drives the indexing mechanism to move one or more blisters into alignment with the piercer and which then moves the mouthpiece relative to the housing so that the piercer pierces the aligned blister(s), wherein the mouthpiece comprises a sleeve,
the housing comprises a chimney which fits closely inside the sleeve
the channel and the channel cover extend inside the chimney, and
the conduit extends through the chimney so that, when the mouthpiece is in the piercing position, the conduit is in fluid communication with the inhalation passage.

The conduit thereby fluidically connects the pressure sensor in the compliance monitor to the inhalation passage in the mouthpiece, whilst allowing the mouthpiece to move relative to the housing in order to pierce the blister.

In a second aspect, the invention provides an inhaler according to the first aspect of the invention and a compliance monitor having a pressure sensor. Preferably the compliance monitor is detachably mountable on the inhaler. When the compliance monitor is mounted on the housing of the inhaler, the pressure sensor is in fluid communication with the inhalation passage via the orifice and the conduit.

The inhaler and/or the compliance monitor may have one or more formations for removably attaching the compliance monitor to the inhaler, such as pegs or clips on the compliance monitor and corresponding holes or slots on the inhaler.

The compliance monitor may have a sealing member which surrounds the pressure sensor.

This provides a seal around the pressure sensor and the orifice when the compliance monitor is attached to the inhaler.

BRIEF DESCRIPTION OF THE FIGURES

The invention will now be further described with reference to the Figures, wherein.

DETAILED DESCRIPTION OF THE INVENTION

The inhaler of the invention has a built-in conduit for connecting the pressure sensor to the inhalation passage, instead of using a separate tube as in WO 16/033421.

Figure 1A:
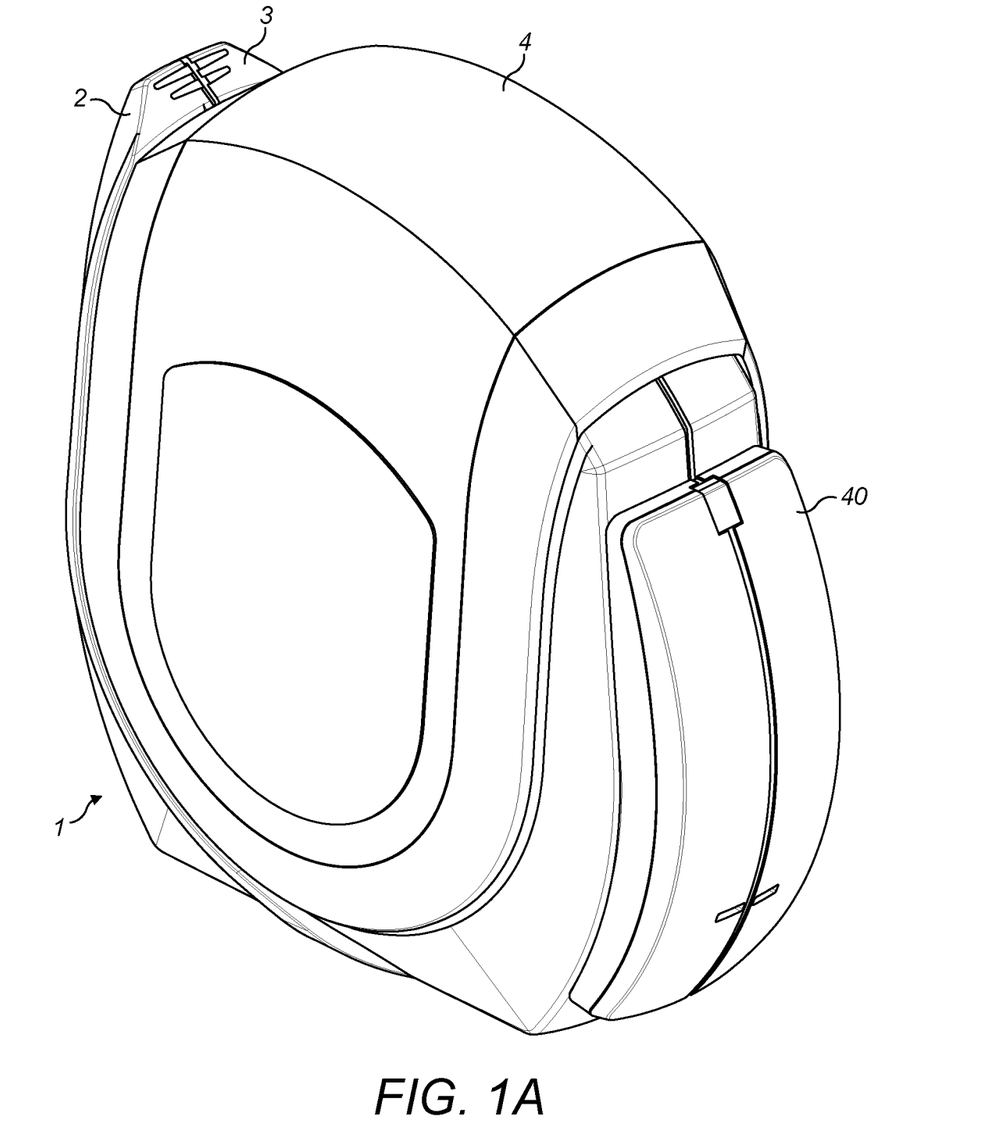
FIG. 1A shows an inhaler according to the invention, with a compliance monitor attached, and with the mouthpiece cover in the closed position.

FIG. 1A shows a dry powder inhaler 1 constructed from two shell parts 2, 3 which are joined together to form a housing which contains a blister strip. A mouthpiece cover 4 is mounted onto the housing. A detachable compliance monitor 40 is attached to one side of the inhaler.

Figure 1B:
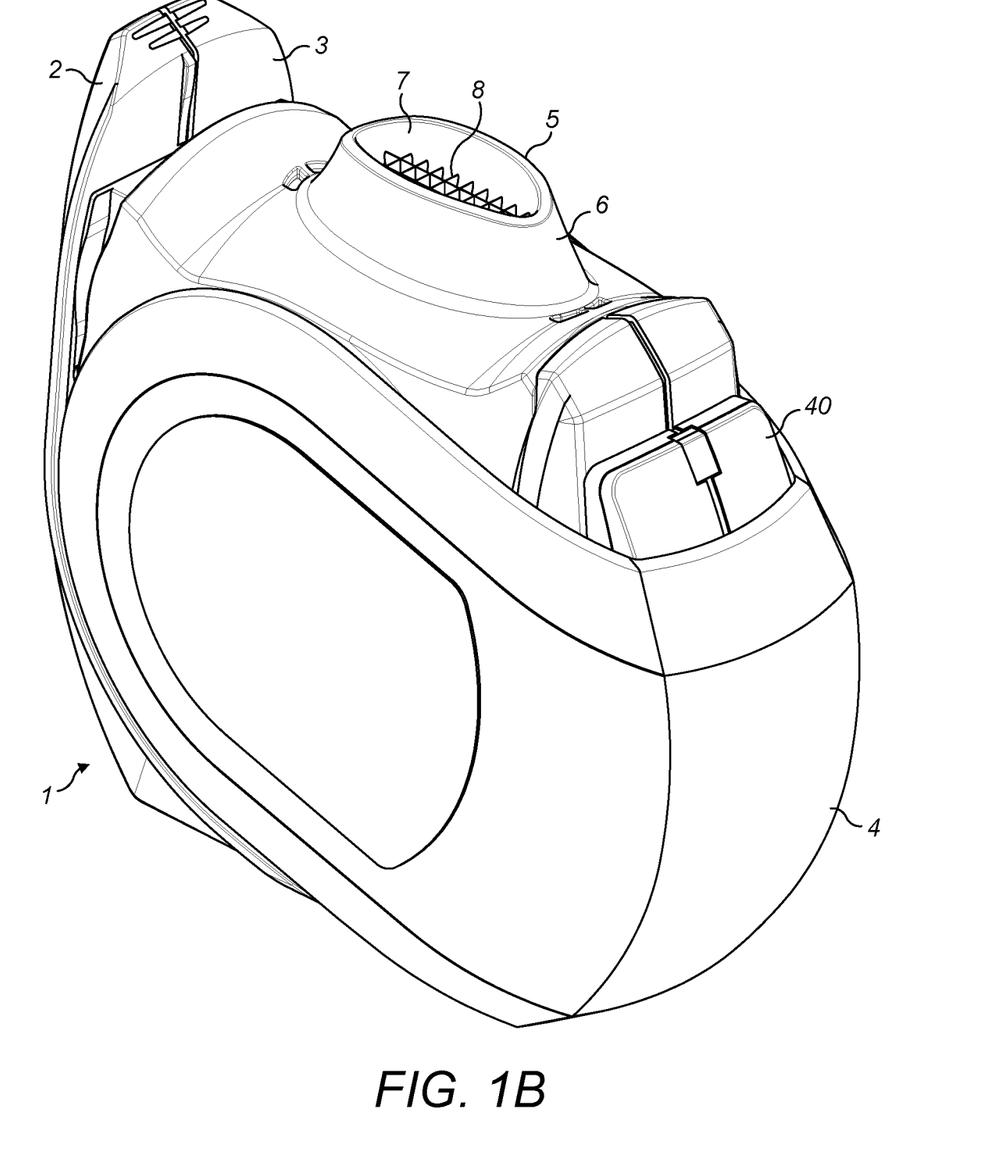
FIG. 1B shows the inhaler of FIG. 1A with the mouthpiece cover in the open position so that the mouthpiece is visible.

The mouthpiece cover 4 can be rotated through approximately 100° from the closed position shown in FIG. 1A, in which it covers and protects a mouthpiece, to a fully open position, shown in FIG. 1B. This exposes the mouthpiece 5 and enables a user to inhale a dose of medicament. The mouthpiece has an external surface 6 which is shaped to fit the user's lips, and an internal surface 7 which defines an inhalation passage through which the aerosolized powder flows. A grid 8 spans the inhalation passage, in order to help deagglomerate the powder and prevent any fragments of the pierced blister from being inhaled.

The mouthpiece 5 is formed as part of a component which is pivotally mounted to the housing. The component includes a piercer (not visible in FIG. 1B) which is located directly beneath the mouthpiece. The inhaler has a gear mechanism that selectively couples the mouthpiece cover to a blister strip indexing mechanism and to the mouthpiece component. Pivoting the mouthpiece cover from the closed position initially causes the indexing mechanism to advance the blister strip. Then, once an unused blister is in position beneath the piercer, the indexing mechanism is disengaged. Moving the mouthpiece cover to the fully open position causes the mouthpiece component to pivot towards the housing so that the piercer pierces the blister. The user inhales through the mouthpiece, which aerosolizes the powder in the pierced blister. This general type of inhaler and its operation is described in detail in WO13/175177. The inhaler may be configured to index and pierce one blister on each actuation. Alternatively, it may index and pierce two (or more) blisters on each actuation. For example, it may deliver two (or more) different formulations or medicaments simultaneously.

Figure 1C:
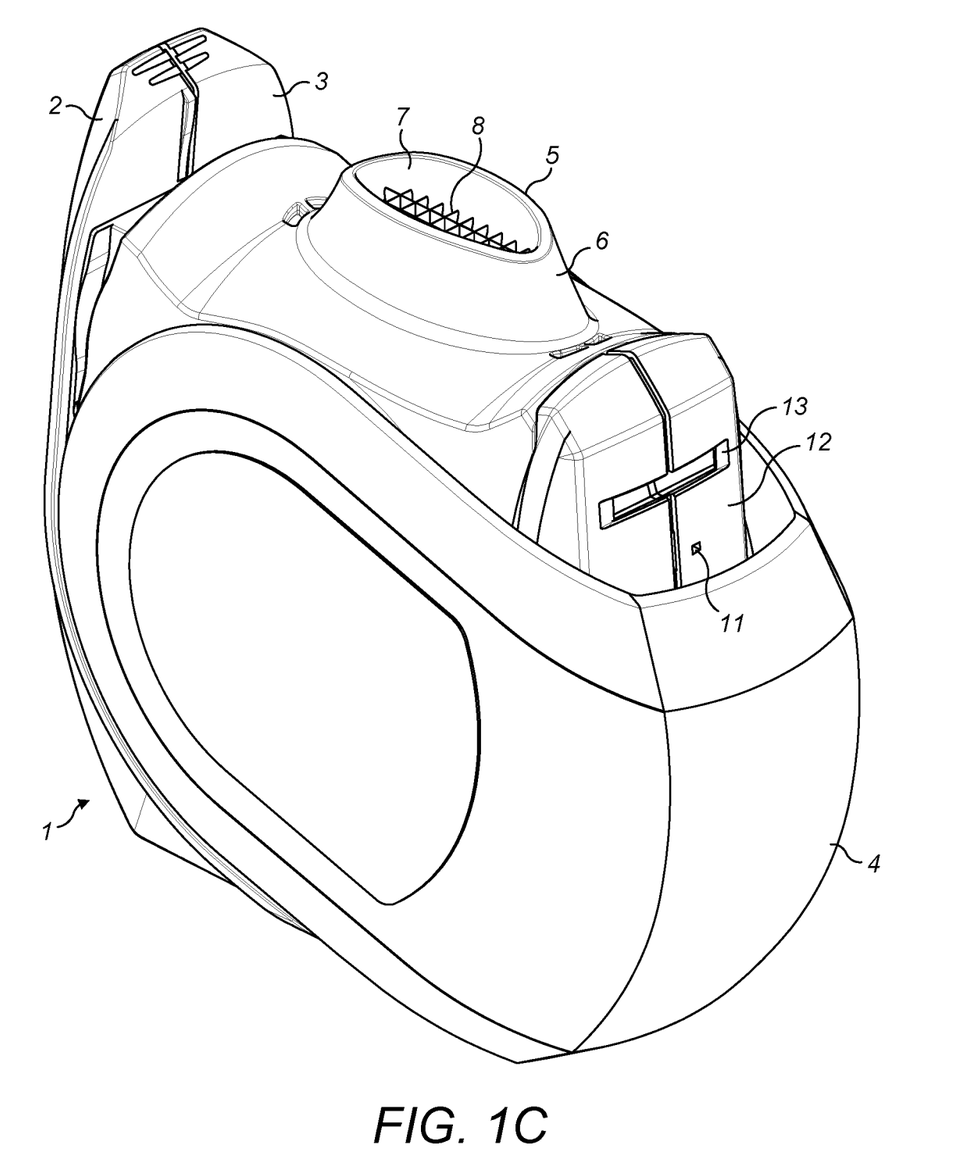
FIG. 1C shows the inhaler of FIG. 1A with the compliance monitor removed and with the mouthpiece cover in the open position.

FIG. 1C shows the inhaler with the compliance monitor having been removed. An orifice 11 is visible in the wall 12 of the housing where the compliance monitor was attached. The orifice 11 leads into a conduit built into the housing. A slot 13 for mounting the compliance monitor is also visible.

Figure 1D:
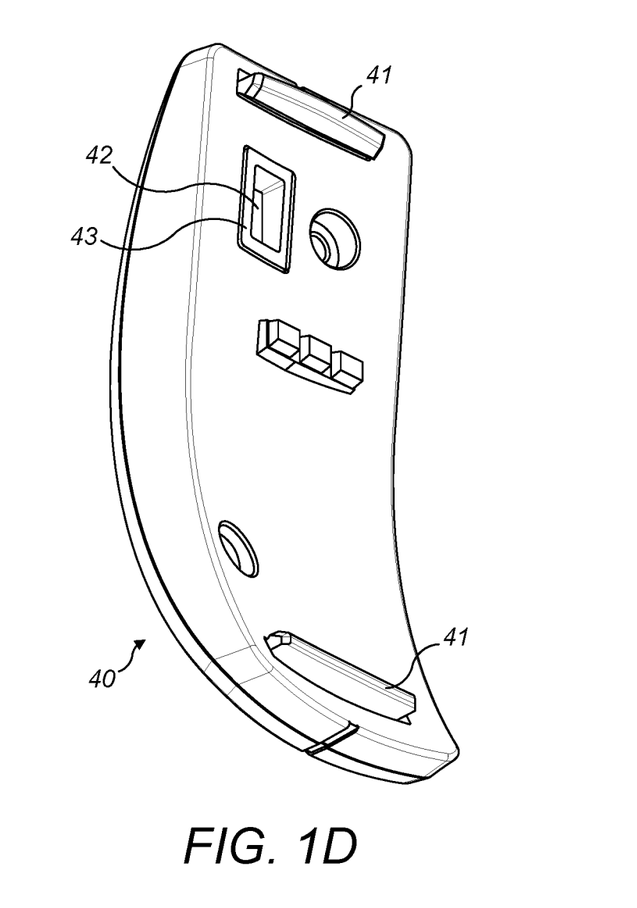
FIG. 1D shows the compliance monitor removed from the inhaler.

FIG. 1D shows the compliance monitor 40 removed from the inhaler. The compliance monitor 40 has two clips 41 which fit into two corresponding slots 13 in the housing (only one of which is visible in FIG. 1C), and thereby hold the compliance monitor in place when mounted on the inhaler. The inside face of the compliance monitor has a recess which contains the pressure sensor 42 and a compliant (e.g. elastomeric) sealing member 43, which surrounds the pressure sensor and protrudes slightly above the top of the recess.

When the compliance monitor is attached to the inhaler, the sealing member abuts and is pushed against the external surface of the housing. The external surface of the housing around the orifice thereby provides a mating surface for the sealing member, so that a seal is formed between the recess in the compliance monitor—which contains the pressure sensor—and the orifice in the housing—which is connected to the inhalation passage in the mouthpiece by the conduit. Thus the pressure at the mouthpiece can be measured during inhalation.

The conduit must satisfy several requirements.

Firstly, the conduit must have a relatively high flow resistance compared to the inhalation flow path. This is necessary to allow the inhaler to be used both with and without the compliance monitor. For example, the user might forget to transfer the compliance monitor from a used-up inhaler to a new one. In the absence of the compliance monitor, the orifice would be open to the external atmosphere and provide an additional air inlet. Unless the flow resistance of the conduit is high, the air flow through the main inhalation passage would be reduced, leading to poor aerosolization of the powder. The flow resistance of the conduit is suitably at least about ten times greater than that of the inhalation flow path. The resistance depends on the length and the cross-sectional area of the conduit. A conduit with a cross-sectional area of less than about 5 $mm^2$, preferably less than 2 $mm^2$, such as about 1 $mm^2$ or less is generally suitable for an inhaler with a typical inhalation flow channel length and width.

Secondly, the compliance monitor must be able to form a leak-free seal with the orifice of the conduit at the external surface of the housing.

Thirdly, it must be possible to manufacture the shell parts and attach them together to form the inhaler, in particular by injection moulding and ultrasonic welding respectively, without significantly increasing the cost or complexity of the manufacturing and assembly process.

A narrow, closed conduit formed entirely within one of the shell parts would be ideal for the first and second requirements, but would be difficult and expensive to mould. The present inventors have solved this problem by identifying a different way to form the conduit. A channel is moulded in one shell part and a corresponding channel cover in the other part, so that a closed conduit is formed when they are joined together.

Figure 2:
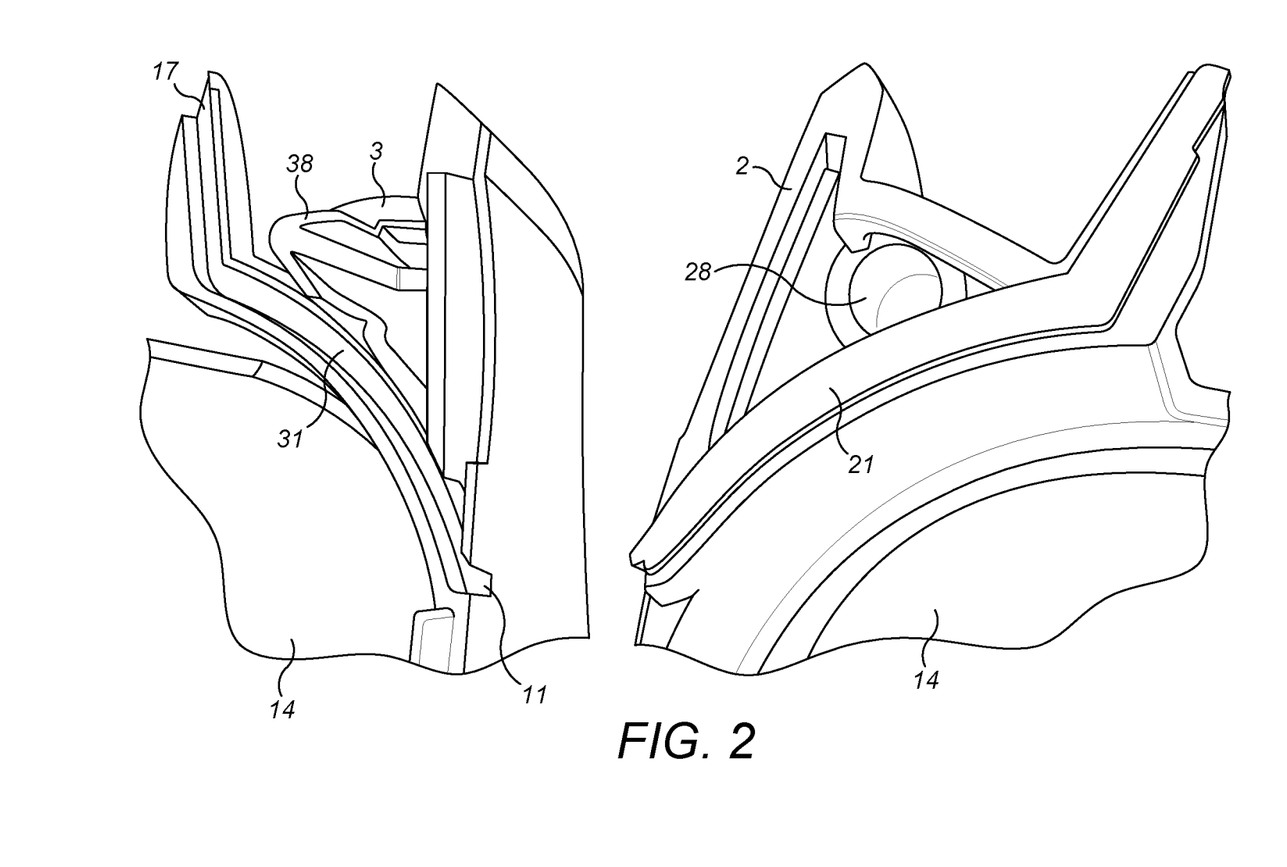
FIG. 2 shows internal views of the regions of the two shell parts of an inhaler according to the invention between the mouthpiece and the orifice.
Figure 3A:
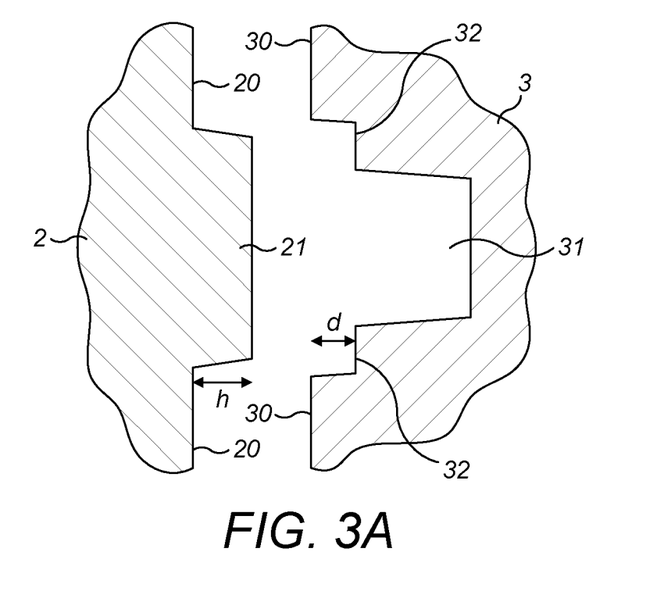
FIGS. 3A and 3B show cross-sections through the shell parts of FIG. 2 in the region of the orifice, before and after being welded together.
Figure 3B:
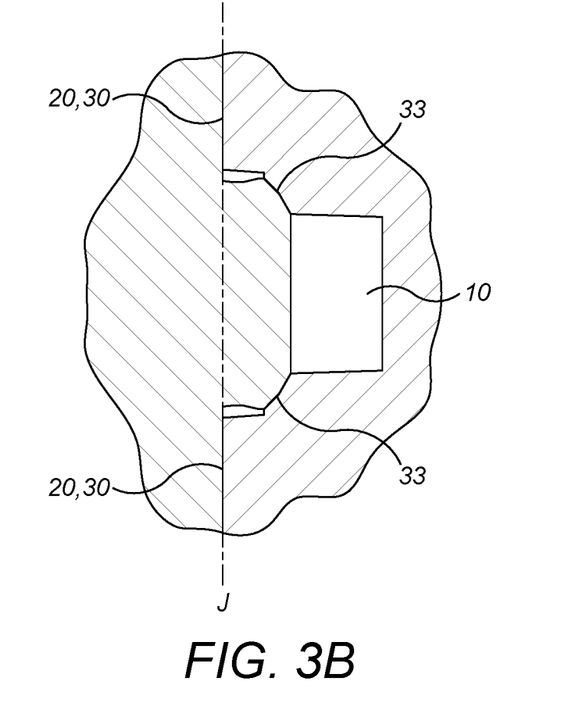
Figure 4:
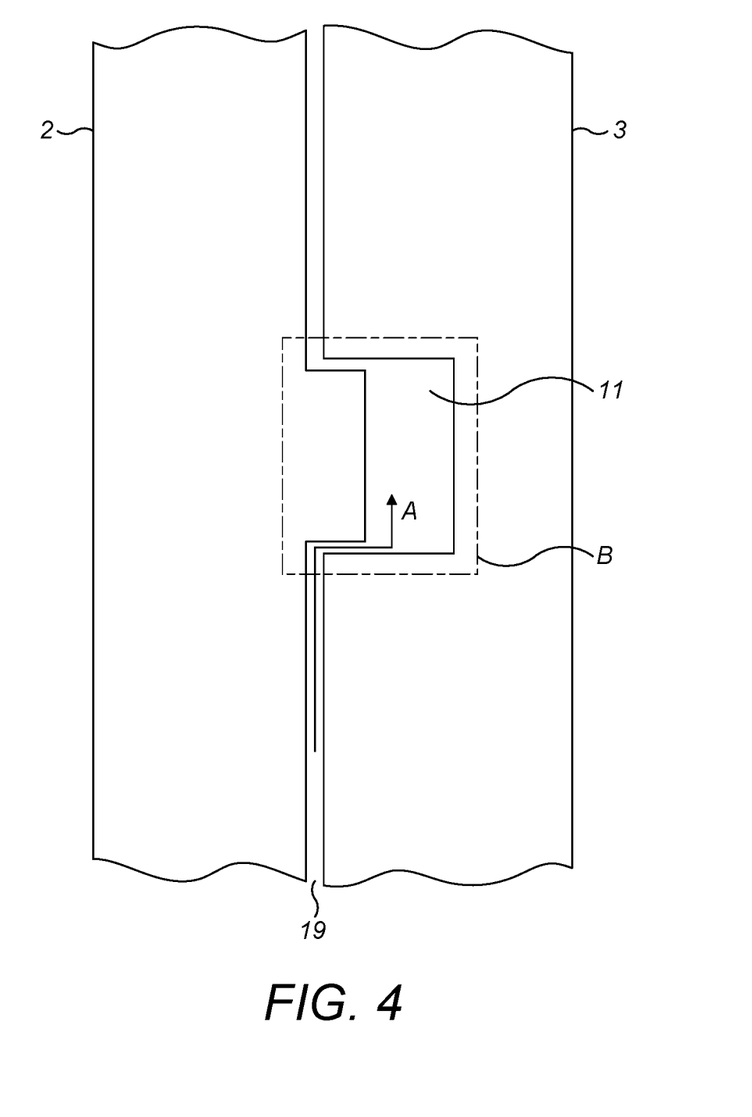
FIG. 4 shows the external surfaces of the shell parts of FIG. 2 in the region of the orifice.
Figure 5A:
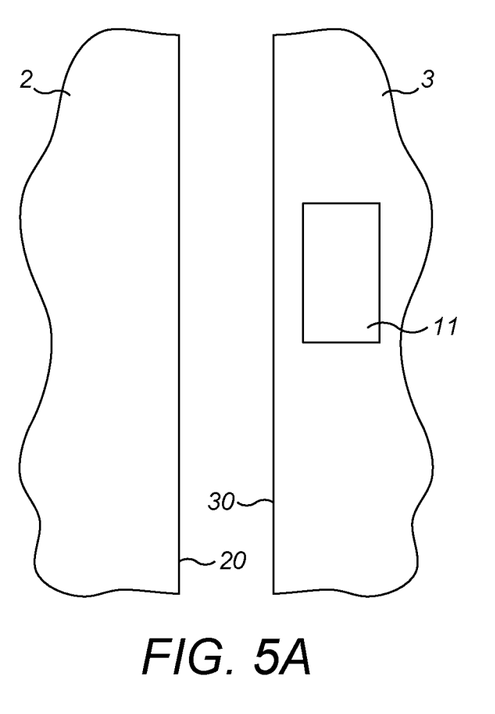
FIGS. 5A and 5B show the external surfaces of the shell parts of a second inhaler according to the invention in the region of the orifice, before and after being welded together.
Figure 5B:
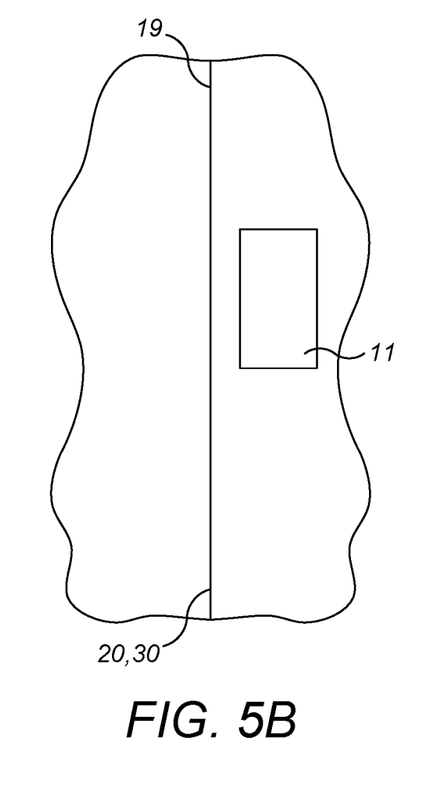

FIGS. 2, 3 and 4 illustrate a first embodiment of an inhaler according to the invention.

FIG. 2 shows internal views of the regions of the shell parts 2,3 between the mouthpiece and the orifice. The shell parts define a compartment 14 for the blister strip (not shown). The second shell part 3 has a cruciform peg 38 and the first shell part 2 has a corresponding hole 28 for receiving the peg 38 when the shell parts are assembled. The second shell part 3 has a channel 31, and the first shell part 2 has a corresponding protrusion 21, which covers the channel to form the conduit when the shell parts are assembled and welded together, as will be described below. One end 17 of the channel, and hence the conduit, opens into the inhalation passage of the mouthpiece (not shown in FIG. 2). The other end forms the orifice 11. The conduit thereby fluidically connects the pressure sensor in the compliance monitor to the inhalation passage in the mouthpiece, so that the pressure can be measured during inhalation.

FIGS. 3A and 3B show the channel 31 and the channel cover 21 in cross-section before and after they have been welded together. The first shell part 2 has a contact surface 20 with a protrusion 21 which forms the channel cover. The second shell part 3 has a contact surface 30 with a corresponding recessed channel 31 with ledges 32 on either side. The protrusion 21 projects by a distance h above the contact surface 20 of the first shell part 2 which is greater than the depth d of the ledges 32 below the contact surface 30 of the second shell part 3. The width of the protrusion is slightly less than the combined width of the channel and ledges.

When the first shell part 2 is placed onto the second shell part 3, the protrusion 21 comes into contact with the ledges 32 which form defined surfaces for welding the channel cover onto the channel. Since h>d, the contact surfaces 20, 30 are spaced apart by a distance (h−d). In other words, there is interference between the protrusion 21 and the ledges 32. This interference provides the material for welding. Ultrasound is applied to the weld surfaces provided by the ledges 32 which causes the plastic to melt to form welds 33. The fact that the combined width of the channel and ledges is greater than the width of the protrusion provides space for redistribution of the interference material as the weld is formed. The contact surfaces 20, 30 then come into contact with each other on the plane J, but are not welded together. If the whole of the contact surfaces were welded, it would be difficult to ensure that the melted plastic would be evenly redistributed so that the surfaces would be completely closed together. The dedicated welding surfaces provided by the ledges focus the energy input for welding over a small area and result in a better seal so that the conduit is airtight along its length.

The welds extend along the length of the channel to form the closed conduit 10. However, it is necessary for the weld to stop before the conduit meets the external surface of the inhaler.

If it did not, the melted plastic would form splay, i.e. excess weld material which is squeezed out along the line where the weld meets the external surface. This splay must be avoided in order to provide a perfectly smooth surface to which the compliance monitor can form a leak-free face seal.

FIG. 4 shows the external surface of the housing in the region around the orifice 11, which is located on the joint 19 between the first 2 and second 3 shell parts. Since there is no weld at the orifice, there is a potential leak path (arrow A) which extends along the joint 19 and into the orifice 11. Thus air could enter the joint outside the region B of the housing which is covered by the sealing member in the compliance monitor (indicated by the dashed line) and travel along the leak path to the orifice. Consequently, the conduit may not provide a completely leak-free, airtight connection to the compliance monitor.

A second embodiment of the invention is illustrated in FIGS. 5 to 9. In this embodiment, the shell parts are designed so that an airtight seal is obtained at the orifice. This is achieved by separating the orifice 11 from the joint 19 between the two shell parts. The orifice is formed entirely within the second shell part, but, crucially, without the conduit being formed entirely within the second shell part. Other than the orifice, the rest of the conduit is formed by the channel cover in the first shell part and the channel in the second shell part as in the first embodiment (i.e. as shown in FIG. 3B). Thus it remains possible to mould the second shell part without significantly increasing the complexity of the moulding process, FIGS. 5A and 5B show the outer surface of the shell parts 2, 3 in the region of the orifice 11 before and after being welded together. The orifice 11 is formed entirely within the second shell part 3. Thus, at the external surface, the there is no protrusion, channel or ledges. Inside the shell parts, the conduit is formed from the channel and channel cover in essentially the same manner as for the first embodiment, but with one important difference, namely that the contact surfaces 20, 30 are separated from the orifice 11. This is achieved in a manner which is described below. The shell parts are not welded at the outer surface as before in order to avoid splay. However, in this embodiment, the potential leak path along the unwelded surface joint does not communicate with the orifice because the orifice is formed entirely within the second shell part. Thus an airtight, leak-free seal can be formed with the compliance monitor.

Figure 6A:
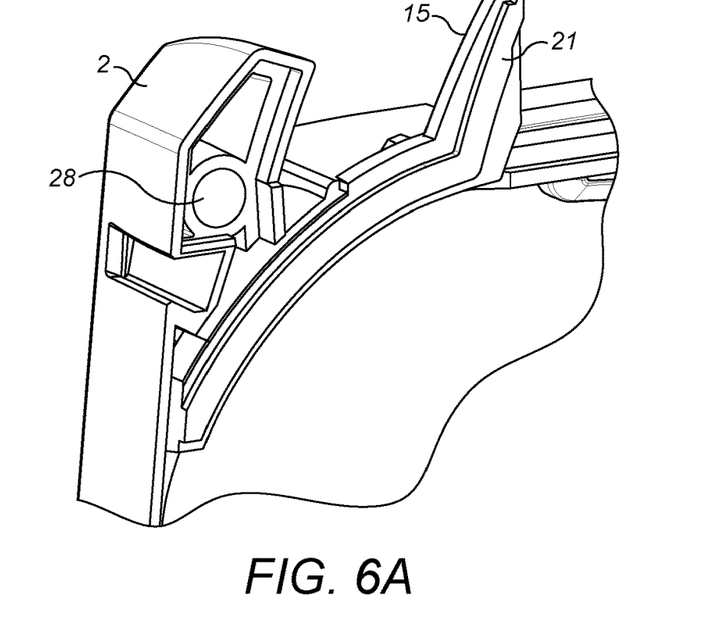
FIGS. 6A and 6B show perspective views of the internal regions of the shell parts of FIG. 5 between the mouthpiece and the orifice.
Figure 6B:
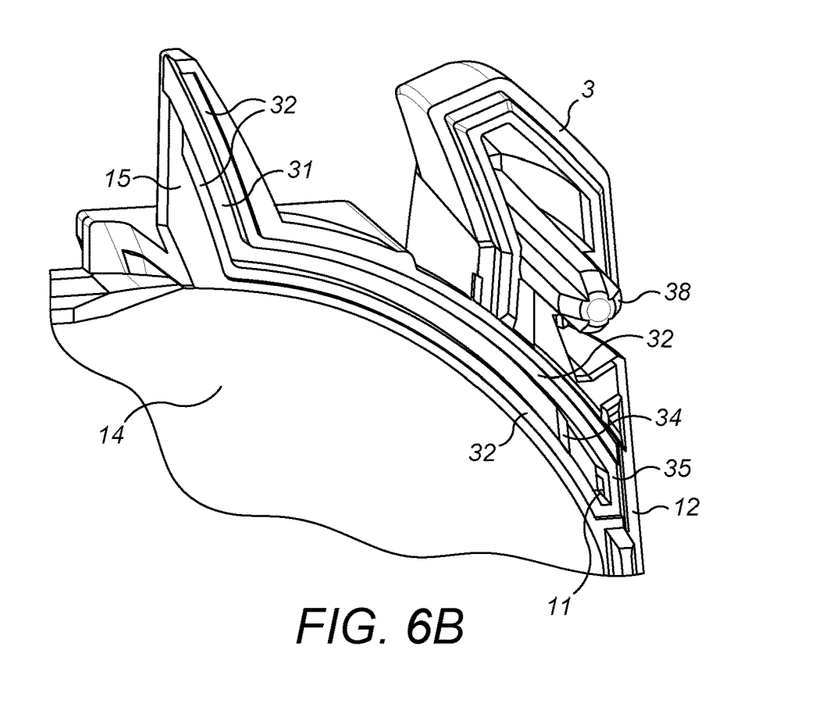

FIGS. 6A and 6B show views of the internal regions of the shell parts which form the channel cover and the channel respectively. The first shell part 2 has a protrusion 21 and the second shell part 3 has a corresponding recessed channel 31 with ledges 32 on either side. The protrusion and channel extend from the orifice 11 which is formed in the wall 12 of the second shell part in a curved shape which follows the perimeter of the blister strip compartment 14, and then in a dog leg up a chimney 15 which fits inside the mouthpiece. Close to the orifice end, the base of the channel has a step 34, so that the depth of the channel is increased. This allows the channel to connect to the orifice which is spaced apart from the contact surface. Instead of having a step, it would be possible for the whole channel to have the same depth as the region adjacent to the orifice, but this would have the disadvantage of increasing the cross-sectional area of the channel, and hence reducing the air flow resistance of the conduit.

As well as the ledges 32 on either side of the channel, there is also an end ledge 35 adjacent to the orifice 11 on the inner side of the wall 12 of the second shell part. The end ledge 35 connects the ledges 32 on each side of the channel so that together they form a continuous weld surface which extends from the mouthpiece end, along one side of the channel, across the end of the channel adjacent to the orifice and back along the other side of the channel to the mouthpiece.

As with the previous embodiment, the protrusion 21 projects above the contact surface 20 of the first shell part 2 by a height which is greater than the depth of the ledges 32 below the contact surface 30 of the second shell part 3. The width of the protrusion is slightly less than the combined width of the ledges and the channel. When the first shell part 2 is placed onto the second shell part 3, the protrusion 21 comes into contact with the ledges 32, 35 which form the dedicated welding surfaces. Since the height of the protrusion is greater than the depth of the ledges, the contact surfaces 20, 30 are initially spaced apart (by a distance equal to the height minus the depth). This interference between the protrusion and the ledges provides the material for welding. Ultrasound is then applied to the weld surfaces provided by the ledges 32, 35 which causes the plastic to melt to form a weld. The fact that the combined width of the ledges and the channel is greater than the width of the protrusion provides space for redistribution of the interference material as the weld is formed. The contact surfaces 20, 30 then come into contact with each other, but are not welded together.

Since the end ledge is inside the second shell part, there is no need to avoid welding in this region, because there is no possibility of splay on the external surface. In principle, the end face of the protrusion could alternatively be welded to the inner side of the wall 12 of the second shell part, so that the end ledge 35 is not required. However, since this weld would lie in the plane perpendicular to the contact surfaces 20, 30, an additional welding step would be required. This would increase the cost and complexity of the assembly process (whereas it is straightforward to mould the end ledge in the second shell part).

The weld extends along the length of the channel, and, unlike the first embodiment, also across the orifice end of the channel. Thus, there is a continuous weld around the channel 31, apart from at the mouthpiece end where it opens into the inhalation passage, for reasons that are explained below. Consequently, it is possible to seal the channel at the orifice end (which prevents a leak path from the joint between the shell parts and the conduit) and to provide a smooth mating surface around the orifice (on which the compliance monitor can form a leak-free face seal), without needing to mould the conduit entirely within the second shell part. It is relatively straightforward to mould the orifice, because the required mould tool part is quite short, whereas moulding the whole conduit would require a long, thin, curved tool part which would increase the cost and difficulty of the moulding process.

In summary, by separating orifice from the joint between the shell parts, so that the weld is separated from the external surface, a leak-free welded conduit can be formed whilst the external surface around the orifice is smooth and flat. Nonetheless, the shell parts can be moulded without significantly increasing the cost and complexity of the mould tool parts.

In principle, the channel could also be welded at the mouthpiece end by means of an end ledge in the same manner as at the orifice. Alternatively the configuration of the first embodiment could be used, but without the need to avoid welding at the end of the channel, because the presence of splay on the inside of the mouthpiece does not cause any difficulties.

However, this is not suitable for some inhalers, such as those described in WO 13/175177. Inhalers of this type have a piercer attached to the underside of the mouthpiece. The mouthpiece moves downwards relative to the housing in order to pierce each blister, and after inhalation moves back up again so that the blister strip can be advanced. Thus, in this type of inhaler, there cannot be a fixed (e.g. welded) connection between the conduit in the housing and the inhalation passage in the mouthpiece.

Figure 7A:
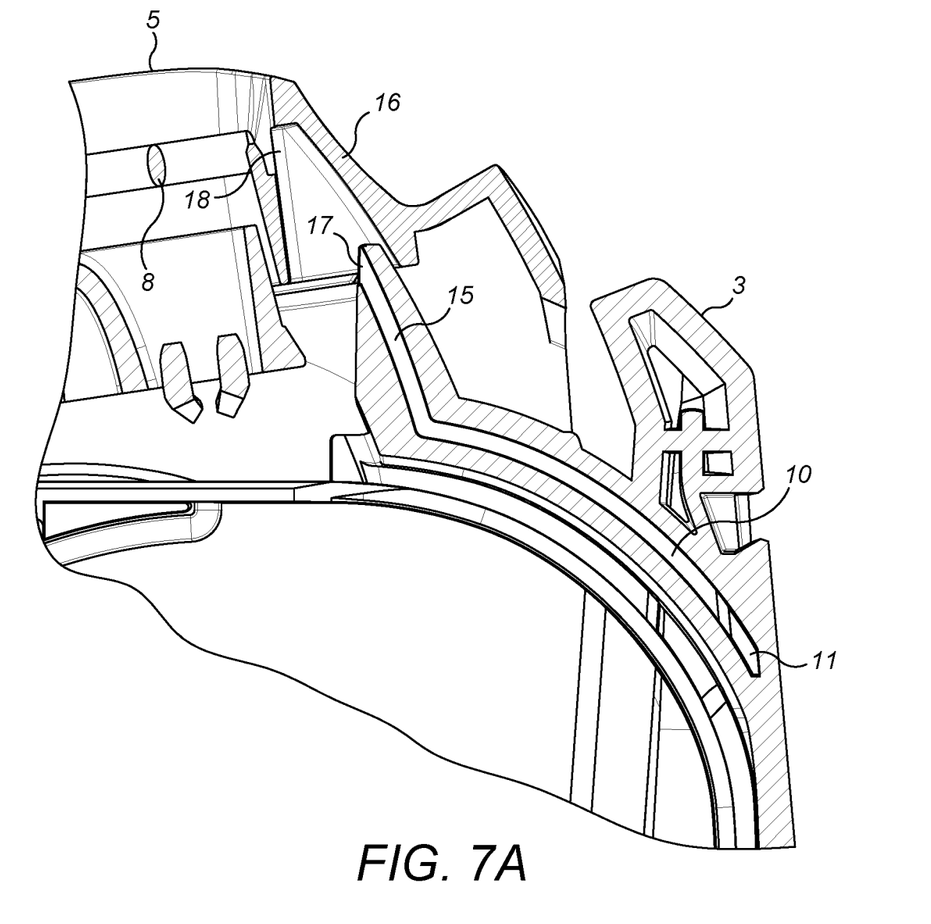
FIGS. 7A and 7B show cross-sections through the mouthpiece and the adjacent region of the second shell part of FIGS. 5A and 5B, with the mouthpiece in the raised and pierced positions respectively.
Figure 7B:
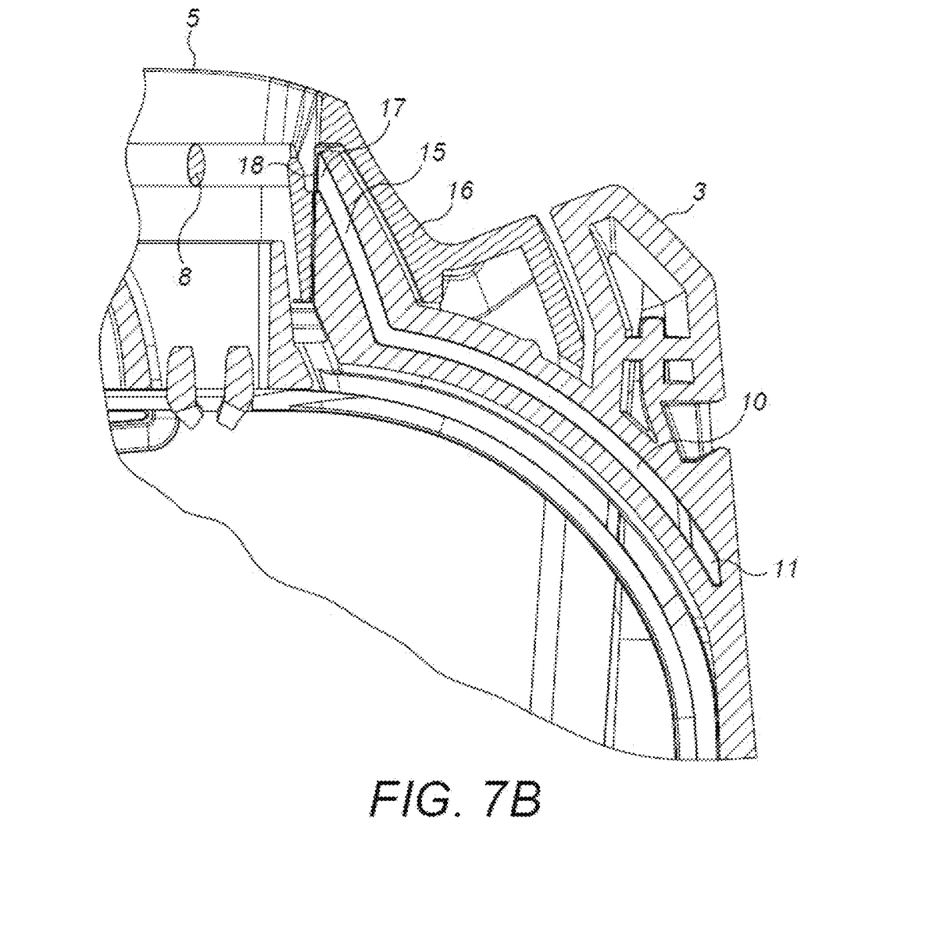

FIG. 7A shows a cross-sectional view of the mouthpiece 5 and the adjacent region of the second shell part 3 with the mouthpiece in the raised position. FIG. 7B is a similar view with the mouthpiece in the pierced position, ready for inhalation. A sleeve 16 is formed within the mouthpiece 5. The right sides (as seen in FIG. 7A) of the chimney 15 and sleeve 16 are arcuate in shape so that the sleeve 16 fits closely around the chimney 15 when the mouthpiece is rotated into the pierced position. The resulting gap between the chimney and the sleeve is narrow and long (i.e. the length of the chimney), so that its air flow resistance is high and the air flow through it is low. This avoids the need for an additional component, such as a moving seal or a flexible tube.

As shown in FIG. 7B, the mouthpiece end 17 of the channel 10 (and hence the conduit) at the top of the chimney 15 is located adjacent to an opening 18 at the top of the sleeve, so that it opens into the inhalation passage in the mouthpiece near the grid 8. The conduit thereby fluidically connects the pressure sensor in the compliance monitor to the inhalation passage in the mouthpiece, so that the pressure can be measured during inhalation. The chimney and sleeve design allows the mouthpiece to move relative to the housing in order to pierce the blister whilst also providing a high resistance leak path.

Figure 8:
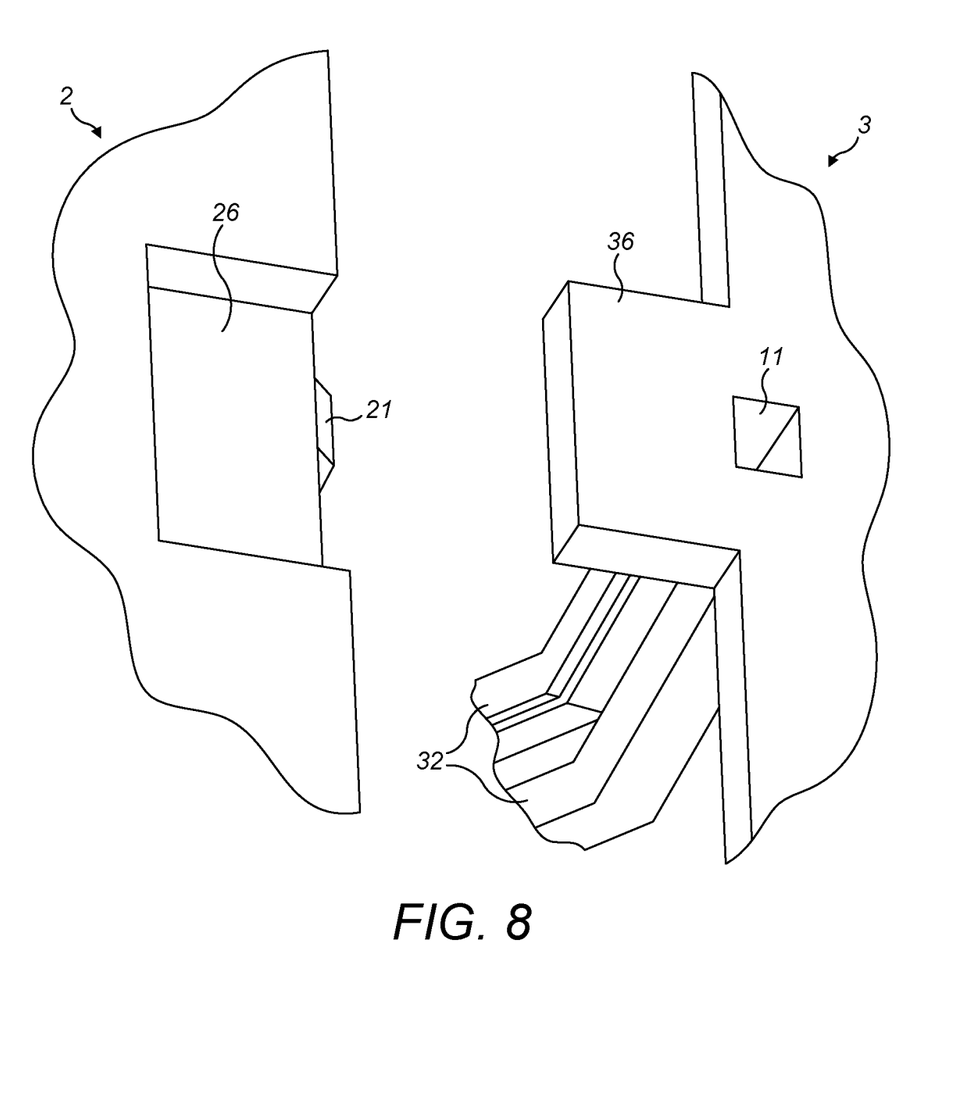
FIG. 8 shows a perspective view of the first and second shell parts of a variant of the second inhaler in the region of the channel and orifice.

FIG. 8 shows a perspective view of the first and second shell parts 2, 3 of a variant of the second embodiment. The conduit is formed by the protrusion 21 and ledges 32 as described above. The difference is that the second shell part 3 has a tab 36 and the first shell part 2 has a corresponding recess 26 into which the tab 36 fits when the shell parts are assembled together. This allows the orifice 11 to be spaced apart from the contact surface without the need to form a step at the orifice end of the channel.

In each of the embodiments described above, the high resistance provided by the narrow conduit allows the inhaler to be used in the absence of the compliance monitor, without a material change in the flow resistance experienced by the user.

The medicament is suitable for administration by inhalation, for example for the treatment of a respiratory disease. It may include one of more of the following classes of pharmaceutically active material: anticholinergics, adenosine A2A receptor agonists, β2-agonists, calcium blockers, IL-13 inhibitors, phosphodiesterase-4-inhibitors, kinase inhibitors, steroids, CXCR2, proteins, peptides, immunoglobulins such as Anti-IG-E, nucleic acids in particular DNA and RNA, monoclonal antibodies, small molecule inhibitors and leukotriene B4 antagonists. The medicament include excipients, such as fine excipients and/or carrier particles (for example lactose), and/or additives (such as magnesium stearate, phospholipid or leucine).

Suitable B2-agonists include albuterol (salbutamol), preferably albuterol sulfate; carmoterol, preferably carmoterol hydrochloride; fenoterol; formoterol; milveterol, preferably milveterol hydrochloride; metaproterenol, preferably metaproterenol sulfate; olodaterol; procaterol; salmeterol, preferably salmeterol xinafoate; carmoterol; terbutaline, preferably terbutaline sulphate; vilanterol, preferably vilanterol trifenatate or indacaterol, preferably indacaterol maleate.

Suitable steroids include budesonide; beclamethasone, preferably beclomethasone dipropionate; ciclesonide; fluticasone, preferably fluticasone furoate; mometasone, preferably mometasone furoate. In one aspect, the method comprises jet milling mometasone, preferably mometasone furoate in the presence of a liquid aerosol.

Suitable anticholinergics include: aclidinium, preferably aclidinium bromide; glycopyrronium, preferably glycopyrronium bromide; ipratropium, preferably ipratropium bromide; oxitropium, preferably oxitropium bromide; tiotropium, preferably tiotropium bromide; umeclidinium, preferably umeclidinium bromide; Darotropium bromide; or tarafenacin.

The active material may include double or triple combinations such as salmeterol xinafoate and fluticasone propionate; budesonide and formoterol fumarate dihydrate glycopyrrolate and indacaterol maleate; glycopyrrolate, indacaterol maleate and mometasone furoate; fluticasone furoate and vilanterol; vilanterol and umclidinium bromide; fluticasone furoate, vilanterol and umclidinium bromide.

The invention claimed is:

1. A dry powder inhaler adapted for detachably mounting a compliance monitor having a pressure sensor, the inhaler comprising:
   a housing comprising a first shell part and a second shell parts,
   a mouthpiece which defines an inhalation passage,
   an orifice in an external surface of the housing, and
   a conduit from the orifice to the inhalation passage which is formed by a channel in the second shell part and a corresponding channel cover in the first shell part, for connecting the pressure sensor to the inhalation passage.

2. The inhaler according to claim 1, wherein the first shell part and the second shell parts are moulded plastic parts.

3. The inhaler according to claim 1, wherein the conduit has a cross-sectional area of less than 5 mm$^2$.

4. The inhaler according to claim 1, wherein the channel has a ledge on each of two opposing lateral sides of the channel.

5. The inhaler according to claim 4, wherein the corresponding channel cover is formed as a protrusion.

6. The inhaler according to claim 5, wherein the protrusion and each ledges are welded together along a corresponding length but are not welded together at the external surface of the housing.

7. The inhaler according to claim 6, wherein a height of the protrusion is greater than a depth of the ledges and a width of the protrusion is less than a width of the channel and the ledges.

8. The inhaler according to claim 4, wherein the orifice is formed entirely within the second shell part.

9. The inhaler according to claim 8, wherein the channel has a step near the orifice so that a depth of the channel is increased.

10. The inhaler according to claim 9, wherein the channel has an end ledge adjacent to the orifice inside of the second shell part, wherein the end ledge connects the ledges on each of the two opposing lateral sides of the channel.

11. The inhaler according to claim 1, wherein the orifice is formed at a joint between the first shell parts and the second shell part.

12. The inhaler according to claim 1, which further comprises a compartment for a blister strip having a plurality of blisters which contain a powdered medicament for inhalation, an indexing mechanism for moving the blister strip, a piercer which is mounted on an underside of the mouthpiece, and an actuator configured to drives the indexing mechanism to move one or more blisters of the plurality of blisters into alignment with the piercer and further to then move the mouthpiece relative to the housing so that the piercer pierces the aligned one or more blister(s) of the plurality of blisters, wherein
   the mouthpiece further comprises a sleeve,
   the housing further comprises a chimney which fits closely inside the sleeve, and
   the conduit extends through the chimney and is configured such that, when the mouthpiece is in the piercing position, the conduit is in fluid communication with the inhalation passage.

13. The inhaler according to claim 1, which further comprises the compliance monitor having the pressure sensor, wherein; the compliance monitor is configured such that upon mounting onto the inhaler, the pressure sensor is positioned in fluid communication with the orifice.

14. The inhaler according to claim 13, wherein the inhaler and/or the compliance monitor further comprise one or more formations for detachably mounting the compliance monitor onto the inhaler.

15. The inhaler according to claim 13, wherein the compliance monitor further comprises a sealing member configured to surround the pressure sensor and to forms a seal with the housing around the orifice when the compliance monitor is mounted onto the inhaler.

16. The inhaler according to claim 1, wherein the conduit has a cross-sectional area of less than 2 mm$^2$.

17. The inhaler according to claim 1, wherein the conduit has a cross-sectional area of about 1 mm$^2$.

* * * * *